July 6, 1948. M. LA PIETRA Plant Pat. 801
APPLE TREE
Filed June 14, 1946
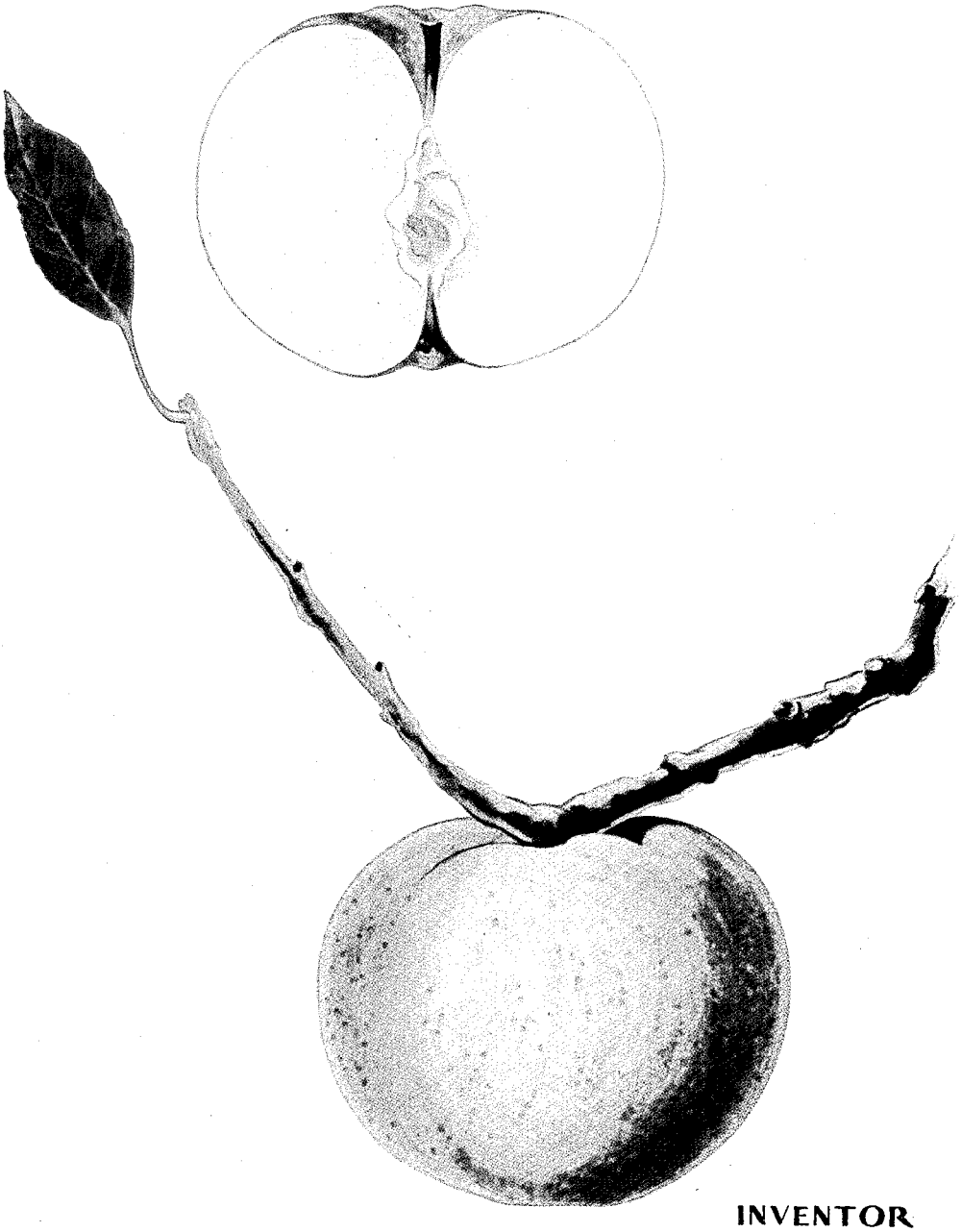
INVENTOR
Marino La Pietra
BY Robert W. Fulwider
ATTORNEY Patented July 6, 1948

Plant Pat. 801

UNITED STATES PATENT OFFICE

801

APPLE TREE

Marino La Pietra, West Los Angeles, Calif.

Application June 14, 1946, Serial No. 676,712

1 Claim. (Cl. 47—62)

The present discovery relates to a new and distinct variety of apple tree, the original of which is a seedling discovered by me in Los Angeles, California.

Cuttings from the original tree have been grafted to various other apple trees and exhibit all the characteristics of the original, including the character and quantity of fruit.

The characteristics of the new variety as determined by careful observation since the discovery of the original seedling in 1935 are specifically set forth hereinafter. The predominating attributes however, which make this new variety of particular value as an all purpose fruit producer are:

1. The substantial seedlessness of the fruit, and the separated carpel therein.
2. The dotted appearance and attractive color of the fruit.
3. A crisp quality and sweet to subacid flavor of the fruit.
4. Its heavy bearing qualities.
5. The ability to prosper and bear heavily in the coastal regions of Southern California.

As previously stated, this new variety of apple tree, the fruit of which is depicted in the accompanying illustration, has been asexually reproduced and observations have determined the characteristics to be permanent.

The following is a detailed description of the new variety based on observations of the original tree and of the grafted cuttings all of which are growing in and around Los Angeles, California.

Dates of first and last picking: Late November to early January. The fruit hangs well and is borne in large clusters with as many as four fully formed apples to a cluster.

Tree: Large; vigorous; heavy foliage; rapid growing; regular and heavy bearing.

Trunk: Medium smooth; grey-green.

Branches: Medium smooth; many; grey-green; tendency to zigzag.

Leaves: In length about 2½"; width about 1"; taper pointed; medium thick; dark green.

*Margin.*—Finely serrate.

*Petiole.*—Length, 1½"; medium thick.

Blossom: Date first blooms—early May; color, white with pinkish tinge disappearing at maturity of blossom.

Fruit: Eating ripe, late November;

*Size.*—Uniform. Axial diameter 3" (mouth of cavity to mouth of basin). Transverse—3¾" (the foregoing are the dimensions of the average of one dozen selected at random).

*Form.*—Oblate.

*Cavity.*—Symmetrical; acute; depth about 1".

*Basin.*—Symmetrical to slightly unsymmetrical; acute conical; non pubescent; depth about ½" (to base of calyx).

Stem: Short, medium-thick, non-pubescent.

Calyx and styles: Open; medium to small (fills about one-half of basin).

Skin: Medium to thin; clings to flesh; dull surface, but wax present takes high polish when rubbed.

*Dots.*—Very conspicuous; very numerous; medium to large; fairly uniform in size; submerged.

*Color of dots.*—Greenish yellow.

*Distribution of dots.*—Fairly uniform, some concentration around basin.

*Color.*—Dark red (4R4/9 to 4R3/7 Munsell, 4L/10 or 5L/10 Maerz and Paul).

*Color distribution.*—Very even, little or no separate ground color.

Flesh: Very juicy; white with greenish or yellowish tint.

*Texture.*—Crisp; fine-grained.

*Flavor.*—Sweet to sub-acid.

*Quality.*—Very good.

Core: Small; axile; elongated axially (extends from cavity to basin).

*Core lines.*—Clasping; fairly distinct.

*Carpel.*—Very distinct; relatively small; elongated axially; readily separated from balance of the fruit.

*Calyx tube.*—Open; medium to small; acute funnel.

*Styles.*—Present but underdeveloped.

*Seed cells.*—Underdeveloped.

*Cell walls.*—Thick and tough.

Seeds: *Number.*—Imperfect, 0 to 1; perfect, none (out of two dozen apples picked at random only one was found having a single imperfect seed, the balance being seedless).

Use: Local market; shipping; dessert; culinary.

Keeping quality: Excellent (storage samples still showed very good eating qualities after three weeks storage in ordinary fruit cooler).

Resistance to insects and diseases: Not well known but believed to be fair to good.

I claim:

A new and distinct variety of apple tree, characterized as to novelty by its ability to grow and bear well in the coastal regions of Southern California, by the seedlessness of its fruit, by its very good crisp, juicy eating quality, by the large size of its fruit, and by its dull-red overall color, substantially as shown and described.

MARINO LA PIETRA.